Figure 1:
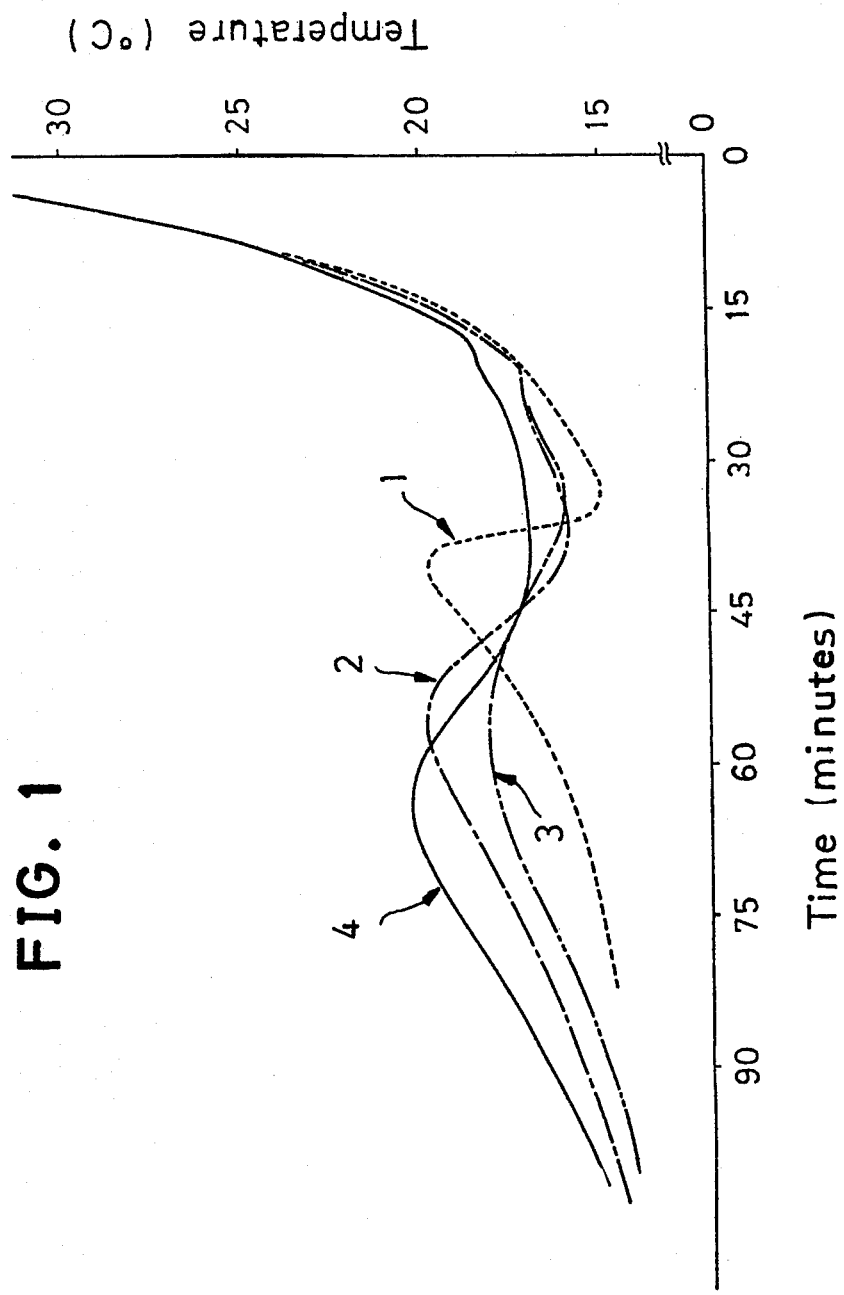

United States Patent [19]

Tatsumi et al.

[11] 4,032,405

[45] June 28, 1977

[54] METHOD FOR PRODUCING CACAO BUTTER SUBSTITUTE

[75] Inventors: Chuji Tatsumi, Sakai; Yukio Hashimoto, Izumiotsu; Masahiko Terashima; Takahal Matsuo, both of Osaka, all of Japan

[73] Assignee: Fuji Oil Company, Ltd., Osaka, Japan

[22] Filed: Apr. 16, 1976

[21] Appl. No.: 677,844

[30] Foreign Application Priority Data

Apr. 17, 1975 Japan .............................. 50-47253

[52] U.S. Cl. .................................. 195/82; 195/30
[51] Int. Cl.² ......................................... C12D 13/08
[58] Field of Search .............................. 195/82, 30

[56] References Cited
OTHER PUBLICATIONS

Whitworth et al., *Process Biochemistry*, 1974 pp. 14–22.

Thorpe et al., *Journal of General Microbiology* (1972), 72, 151–163.
Cook, *The Chemistry and Biology of Yeasts* (1958) pp. 198–202.
Watanabe, *Chemical Abstracts* vol. 68 (1968) 70389m.

*Primary Examiner*—Lionel M. Shapiro
*Attorney, Agent, or Firm*—Wenderoth, Lind & Ponack

[57] ABSTRACT

A method for producing a cacao butter substitute which comprises cultivating a microorganism capable of producing fats and oils rich in 1,3-disaturated-2-unsaturated-triglycerides belonging to the genus *Endomyces, Rhodotorula, Lipomyces* or *Rhodosporidium,* such as *Endomyces vernalis, Rhodotorula gracilis, Rhodotorula glutinis, Rhodotorula graminis, Rhodosporidium toruloides, Lipomyces starkeyi* and *Lipomyecs lipofer,* under an aerobic condition, collecting the cells, isolating fats and oils rich in 1,3-disaturated-2-unsaturated-triglycerides from the cells, and optionally subjecting the fats and oils to fractionation.

5 Claims, 1 Drawing Figure

METHOD FOR PRODUCING CACAO BUTTER SUBSTITUTE

The present invention relates to a method for producing fats and oils by a fermentation process. More particularly, it relates to a method for producing a cacao butter substitute which is usually called "hard butter" or "hard fat" by cultivating a certain microorganism and collecting fats and oils rich in 1,3-disaturated-2-unsaturated-triglycerides from the cells thereof.

It is well known chocolate is one of the important materials for confectionery and that the chocolate has such unique characteristics that it is solid at room temperature but when it is kept in the mouth, it melts, which characteristics are due to the specific glyceride components of cacao butter contained in the chocolate. The cacao butter contains a large amount of 1,3-disaturated-2-unsaturated-triglycerides (hereinafter, referred to as "$S_2U$"), for instance, 24.2% by weight of 1,3-distearoyl-2-oleoyl compound (hereinafter, referred to as "SOS"), 32.8% by weight of 1-stearoyl-2-oleoyl-3-palmitoyl compound or 1-palmitoyl-2-oleoyl-3-stearoyl compound (hereinafter, referred to as "POS") and 12.1% by weight of 1,3-dipalmitoyl-2-oleoyl compound (hereinafter, referred to as "POP") [cf. J. Sampuguna et al; Lipids, Vol. 4, page 444 (1969)]. However, the cacao butter is harvested from nature and is very expensive. Furthermore, the cacao butter has a fixed melting point: 34° – 35° C, but on the other hand, the suitable melting properties of chocolate vary with the season, region, or the like, and therefore, it is difficult to provide the cacao butter having the most suitable melting properties for the individual chocolate. Accordingly, there have been proposed various cacao butter substitutes having similar melting properties to those of the natural cacao butter. One of the cacao butter substitutes is $S_2U$-rich fats and oils, such as vegetable butters (e.g. shea butter, illipe butter, Borneo tallow, phulwara butter, or kokum butter) or palm oil, which may be used as it is or after being fractionated, and another one is the product obtained by hydrogenating a liquid oil (e.g. peanut oil), followed by, if desired, fractionation thereof.

According to the first proposal, the substitute can be admixed with the cacao butter in any optional ratio to give an excellent product (subject to the high content of the $S_2U$ components), since the substitute has macroscopically similar glyceride components to those of the cacao butter. However, since this substitute is also a natural product, there are the same problems as in the cacao butter. Particularly, the commercially used starting materials for the vegetable butter, i.e. Butyrospermum parkii (the starting plant for shea butter) and Madhuca longifolia (the starting plant for illipe butter) are wild plants, and it is very difficult to get the starting materials because the harvest thereof depends on the harvest of the fruits and further because of the recent instability of the political situation and nationalism in the producing countries (i.e. the developing countries in the torrid zone).

According to the second proposal, the starting materials can be easily obtained because they are produced in various countries in the world. However, this substitute can hardly be admixed with the cacao butter because the glyceride components of the substitute are insignificantly different from those of the cacao butter. Accordingly, when this substitute is used, there can not be obtained the desired chocolate having the excellent melting properties as the product produced by using the natural cacao butter, and therefore, this substitute is not a true cacao butter substitute.

Under the circumstances, it has been desired to more easily obtain the excellent cacao butter substitute having similar glyceride components to those of the natural cacao butter without relying on the wild plants in the torrid zone. As the result of the extensive studies by the present inventors, it has now been found that the desired cacao butter substitute can be obtained by a fermentation process.

The fermentation process has been remarkably developed in various fields, such as the production of antibiotics, enzymes, amino acids, proteins, or the like, but has not yet been developed in the field of fats and oils, notwithstanding the fact that it is well known that various microorganisms, such as fungi, bacteria, yeasts or algae can accumulate fats and oils as the metabolite in their cells in such a large amount as 50 to 60% by weight, occasionally about 80% by weight. The main reasons why the fermentation process has not been applied to the production of fats and oils may be that the fermentation process is very expensive and the product can not be compete with the commercially available, animal and vegetable fats and oils in price, and further that the fermentaion fats and oils have various components and occasionally contains a high ratio of the fatty acids having an odd number of carbon atom which are considered unsuitable for foodstuffs.

However, according to the present inventors' study, it has unexpectedly been found that certain microorganisms can produce the desired, $S_2U$-rich fats and oils in a high yield and that the fats and oils thus obtained are suitable for the cacao butter substitute.

An object of the present invention is to provide a method for producing a cacao butter substitue by a fermentation process.

Another object of the invention is to provide $S_2U$-rich fats and oils useful for the cacao butter substitute in a high yield and at a low cost.

These and other objects of the invention will be made apparent from the following description.

As the result of the extensive studies on the relationship between the microorganisms and the produced fats and oils, it has been found that certain microorganisms of the genera Endomyces, Rhodotorula, Lipomyces and Rhodosporidium can produce a large amount of $S_2U$-rich fats and oils. For instance, *Rhodosporidium toruloides* IFO 0413 can produce the fats and oils having the fatty acid components as shown in Table 1.

Table 1

| Carbon number | $C_{14}$ | $C_{16}$ | $C_{16}$–$C_{18}$ | $C_{18}$ | $C_{18}:1^{*1}$ | $C_{18}:2^{*2}$ | $C_{20}$ | $C_{18}:3^{*3}$ |
|---|---|---|---|---|---|---|---|---|
| Content (% by weight) | 1.3 | 25.0 | 0.9 | 12.7 | 46.4 | 11.7 | 0.1 | 2.1 |

[Note]:
*1 $C_{18}:1$ means the fatty acid has 18 carbon atoms and one double bond in the molecule.
*2 $C_{18}:2$ means the fatty acid has 18 carbon atoms and two double bonds in the molecule.
*3 $C_{18}:3$ means the fatty acid has 18 carbon atoms and three double bonds in the molecule.

When the fats and oils are analyzed with respect to the triglyceride components by a pancreatic lipase method (cf. J. Amer. Oil Chem. Soc., Vol. 41, pages 693 – 696), they contain POP: 19.3% by weight, POS: 22.2% by weight, SOS: 6.4% by weight (the total $S_2U$: 47.9% by weight), trisaturated triglycerides: 2.5% by weight, diunsaturated triglycerides: 39.6% by weight, and 1- or 3-monounsaturated triglycerides: 2.1% by weight. Accordingly, the fats and oils can be used as the cacao butter substitute as they are, although if they are once fractionated to remove the compounds having a low melting point, the resultant product is more suitable for the cacao butter substitute. Likewise, another strain, *Rhodosporidium toruloides* IFO 0559, can produce the fats and oils having the similar fatty acid components and the triglyceride components as shown in Table 2.

Table 2

| Fatty acid components: Carbon number | $C_{14}$ | $C_{16}$ | $C_{16}$–$C_{18}$ | $C_{18}$ | $C_{18}$:1 | $C_{18}$:2 | $C_{20}$ | $C_{18}$:3 |
|---|---|---|---|---|---|---|---|---|
| Content (% by weight) | 2.7 | 30.7 | 0.3 | 10.8 | 49.2 | 4.0 | 0.1 | 1.1 |

| Triglyceride components: Component | POP | POS | SOS | Trisaturated | Diunsaturated | 1- or 3- monounsaturated |
|---|---|---|---|---|---|---|
| Content (% by weight) | 17.6 | 15.2 | 3.8 | 3.6 | 43.6 | 4.1 |

The microorganisms used in the present invention include various species of the genera Endomyces, Rhodotorula, Lipomyces and Rhodosporidium. However, from the practical viewpoint, the microorganisms should be capable of accumulating a large amount of fats and oils, which are preferably rich in the $S_2U$ components, in the cells.

Suitable examples of the microorganisms are *Endomyces vernalis*, *Rhodotorula gracilis*, *Rhodotorula glutinis*, *Rhodotorula graminis*, *Rhodosporidium toruloides*, *Lipomyces starkeyi*, and *Lipomyces lipofer*. These microorganisms belong to Ascomycetes and Basidiomycetes in Fungi and to Cryptococcales or Moniliales in Imperfect Fungi, and they are usually called yeasts.

These microorganisms may be stock cultures deposited in various depositories in the world, for instance, CBS (Central Bureau voor Shimmelcultures, Baarn, Netherland), NRRL (Northern Utilization Research and Development Division, U.S. Department of Agriculture, Peoria, Ill.), ATCC (American Type Culture Collection, Md.), IFO (Institute for Fermentation, Osaka, Japan), IAM (Institute of Applied Microbiology, University of Tokyo, Tokyo Japan), BIKOKEN (Fermentation Research Institute, Agency of Industrial Science and Technology, Chiba city, Japan), AHU (Faculty of Agriculture, Hokkaido University, Sapporo, Japan), OUT (Faculty of Engineering, Osaka University, Osaka, Japan), AKU (Faculty of Agriculture, Kyoto University, Kyoto, Japan), NCYC (National Collection of Yeast Cultures, Brewing Industrial Research Foundation, Natfield, England), and IMAB (Instituto de Microbiologia Agricola, Buenos Aires, Argentina), from which the culture can be easily obtained. Besides, the microorganisms may also be isolated from natural origins, for instance, leaves or stalks, etc. of vegetables or the like.

The selection of the suitable microorganisms may be carried out by measuring the quantity of the $S_2U$ contents in the microorganism cells. It may be favorable to subject the microorganisms to preliminary screening, such as a gas chromatography, whereby the microorganisms capable of producing a large amount of saturated fatty acids having 16 or 18 carbon atoms ($C_{16}$:0 or $C_{18}$:0) and monounsaturated fatty acids having 18 carbon atoms ($C_{18}$:1) are elected. From the industrially practical viewpoint, it is preferable that the cells contain 30% by weight or more of the fats and oils, wherein the yield of the fats and oils on the basis of the glucose (so-called "Fat coefficient") is 10% by weight or more and the $S_2U$ contents in the fats and oils are 30% by weight or more (or $C_{16}$:0 or $C_{18}$:0 contents: 30% by weight or more, and $C_{18}$:1 contents: 15% by weight or more). The microorganisms may also be mutated by conventional mutating means, for instance, X-ray irradiation, γ-ray irradiation, treatment with nitrogen mustards, treatment with metabolic antagonists, or the like, by which the capacity of the production of the desired fats and oils may be increased.

Examples of the stock cultures used in the present invention are as follows:

*Endomyces vernalis*: IFO 0114,

*Rhodosporidium torulides*: IFO 0413, IFO 0559, IFO 0871, IFO 0880, IFO 1236, IFO 8766, and IFO 8767,

*Rhodotorula glutinis*: IFO 0695, IFO 1005, IFO 1501, IFO 1503, IFO 1535, IAM 4007, IAM 4387, IAM 4427, IAM 4459, IAM 4492, IAM 4550, IAM 4614, IAM 4630, IAM 4653, IAM 4686, IAM 4272, IAM 4747, IAM 4812, IAM 4906, IAM 4918, AHU 3942, AHU 3943, AHU 3944, OUT 6150, OUT 6151, CBS 20, CBS 323, CBS L-324, IMAB L-4-2, NCYC 59, NRRL Y-842, NRRL Y-1586, and NRRL Y-1587,

*Rhodotorula graminis*: IFO 1422, and NCYC 502,

*Lipomyces lipofer*: IFO 0673, CBS 944, ATCC 10742, and AKU 4420, and

*Lipomyces starkeyi*: IFO 0678, CBS 1807, and IAM 4753.

According to the present invention, firstly, the microorganism is cultivated in a usual manner.

That is, a strain capable of producing $S_2U$-containing fats and oils is inoculated in an appropriate medium and then cultivated under an aerobic condition at a temperature suitable for the growth of the microorganism. The shaking culture is more preferable than the stationary culture since the microorganisms are aerobic. In the industrial production, it is preferable to cultivate the microorganism in a liquid medium with aeration and agitation therein.

The medium contains assimilable nitrogen and carbon sources and further essential inorganic salts, such as potassium, sodium, calcium, magnesium, iron, zinc, manganese, copper, etc. Moreover, minor organic nutrients, such as vitamins, amino acids, or the like may be occasionally required, depending on the kind of microorganism.

As the nitrogen sources, organic nitrogen sources, such as asparagine, glutamine, and peptone, are particularly suitable, but there may also be used inorganic nitrogen sources, such as ammonium sulfate, ammonium nitrate, urea (in case the microorganism has an urease activity), or the like, which are cheaper than the organic nitrogen sources.

The carbon sources include, preferably, pentoses (e.g. xylose), hexoses (e.g. glucose, or fructose), disaccharides (e.g. sucrose, or maltose), or the like, but other saccharides, such as oligosaccharides (e.g. raffinose, or stachyose) and water-soluble polysaccharides (e.g. soluble starches, or dextrine) may also be assimilated by some microorganisms. Moreover, other assimilable liquid or gaseous hydrocarbons and lower fatty acids (e.g. acetic acid salt) may optionally be used. In the industrial production, it is preferable to use various wastes rich in assimilable carbon sources. Suitable examples of the wastes are sulfite pulp waste liquors, wood saccharification waste liquors, blackstrap molasses, cannery waste liquors, soybean protein extraction liquors (i.e. soybean whey), cheese production liquors (i.e. cheese whey), starch production liquors (e.g. corn starch production liquor), butchery waste liquors, or the like. Among these waste liquors, blackstrap molasses (e.g. sugar production liquors, particularly sucrose production liquor) and corn starch production liquor are preferable, because they contain a large amount of organic or inorganic minor nutrients, useful for the growth of the microorganisms, as well as the saccharides. Besides, meat extracts, corn steep liquor, or yeast extracts are useful as the minor nutrient.

These nitrogen and carbon sources, inorganic salts and other nutrients as mentioned above are incorporated into the medium in the optimum amount so that the microorganisms can be grown in the best way. The optimum amount of the nutrients may vary with the kind of the microorganisms, but is usually C: 0.8 to 5.0% by weight and N: 0.006 to 0.17% by weight on the basis of the total weight of the medium. Particularly, the C/N ratio is important for the growth of the microorganisms and should be determined after careful experiments. When the C/N ratio is decreased by the decrease of carbon sources, it results in the remarkable decrease of the fats and oils contents and also the $S_2U$ contents in the product. When the nutrients are used in an ideal C/N ratio, the cells of the microorganism are obtained in a higher yield and further the contents of the fats and oils and also the $S_2U$ are increased.

The cultivation is usually carried out at a temperature of from 20° to 37° C, preferably from 25° to 30° C. It has been found that when the cultivation temperature is higher, the contents of the saturated glycerides in the fats and oils contained in the cells are increased, within the temperature range at which the microorganism grows well. Accordingly, it is preferable to cultivate the microorganism at a higher temperature for increasing the yield of the $S_2U$ contents. The cultivation at a high temperature is also preferable from the viewpoint of the industrial production, because the fermentation temperature can be more easily controlled at a higher temperature.

The cultivation is usually carried out within 48 hours. When the cultivation is carried out for 60 hours or more, it is not only uneconomical, but also results in the decrease of the fats and oils contents in the cells, because the produced fats and oils are hydrolyzed to give the undesirable by-products, such as di- and monoglycerides and free fatty acids. However, on a small scale, the cultivation time may be somewhat extended and may occasionally be about 90 hours or more, depending on the kind of the microorganisms.

The isolation of the desired fats and oils from the cells thus obtained is carried out as follows.

The culture broth is firstly filtered or centrifuged to collect the cells. In this case, it is preferable to make the broth acidic for making the filtration easier. The wet cells thus collected are ground with a colloid mill or a ball mill, and then extracted with an appropriate solvent (e.g. n-hexane). Alternatively, the collected cells are freeze-dried or spray-dried and then the fats and oils are pressed out with a cage press or an expeller, or extracted with a solvent (e.g. n-hexane). Alternatively, the wet cells are frozen to break the cell membrane and returned to room temperature, and then the fats and oils are extracted with a solvent. Moreover, for making the extraction easier, the cells may previously be treated with an ultrasonic wave to break the cell membrane or be treated with a hemicellulase, etc. to remove the cell membrane. On an experimental scale, the wet cells may simply be ground with quartz sand or glass pellet in a mortar. The residual cells obtained after extracting the fats and oils are rich in proteins, vitamins, and enzymes, and therefore, they are useful as a feed for animals, and further are used as a protein source for human beings after extraction and are also used as a starting material for medicines.

The fats and oils thus obtained contain various impurities, such as mono- or di-glycerides, free fatty acids, phytosterols, phospholipids and carotenoids, and therefore, are subjected to refining for removing the impurities. The refining is carried out by a conventional method, i.e. by subjecting to deacidification, decolorization and deodorization in a conventional manner. The refining includes an alkali refining and a physical refining (cf. *Bailey's Industrial Oil and Fat Products*, third edition, edited by Daniel Swern, pages 719 – 784, and Physical Refining of Oils and Fats by G. B. Martinenghi, Corbella, Milano, 1971). The alkali refining is carried out by removing the gummy materials with a degumming agent, such as citric acid or phosphoric acid, adding to the resultant product an alkaline solution (e.g. NaOH solution) to react it with free fatty acids contained in the crude fats and oils, centrifuging it to remove the produced fatty acid soap, adding to the resulting product deacidified fats and oils and an adsorbent (e.g. activated clay or activated carbon), heating the mixture at about 110° C under reduced pressure, filtering the resulting mixture with a filter press to remove the adsorbent, heating the resulting decolorized fats and oils at about 240° C, and blowing steam therein to remove the odorous materials. The physical refining is carried out by degumming and decoloring in the same manner as described above, and then subjecting the fats and oils thus treated to a steam distillation under reduced pressure, whereby the deacidification and the deodorization are performed at one time.

The refined fats and oils thus obtained may be used as the cacao butter substitute as they are, but it is preferable to subject them to fractionation for enhancing the $S_2U$ contents.

For the fractionation, there may be used a wintering method wherein the fats and oils are merely separated into the solid fraction and the liquid fraction by cooling thereof; a wet wintering method wherein the fats and oils are dispersed into an aqueous solution of a surfactant and the mixture is cooled to separate it into the crystalline (solid) fraction, the liquid fraction and the aqueous layer; or a solvent fractionation method wherein the fats and oils are dissolved in an organic solvent and the mixture is cooled stepwise to separate it into various fractions having various melting points. The most preferred one is the solvent fractionation method, by which the desired fraction containing a large amount of $S_2U$ components can be easily obtained by selecting a suitable kind and amount of the solvent. The solvent includes all kinds of solvents useful in the conventional solvent fractionation method, such as n-hexane, methyl ethyl ketone, acetone, ethanol, or the like.

The fractionation may usually be carried out by the following steps: (1) removing the trisaturated triglycerides having a higher melting point by precipitating them from the mixture (when trisaturated triglycerides are contained in a large amount, the viscosity of the chocolate is increased, which results in difficulty in tempering thereof), (2) separating the desired 1,3-disaturated-2-monounsaturated triglycerides fraction as the second precipitate, and (3) removing the liquid fraction containing monosaturated-diunsaturated and triunsaturated triglycerides. When the content of the trisaturated triglycerides is very small, the first step may be omitted. This fractionation may be occasionally carried out prior to the deodorization step in the refining procedure.

The fats and oils suitable for the cacao butter substitute contain the $S_2U$ components of at least 15% by weight, preferably 25% by weight or more.

The fats and oils thus fractionated have excellent characteristics for the cacao butter substitute. For instance, the fractionated fats and oils (12 g) obtained in Example 1 described hereinafter are added to a test tube (inside diameter: 16.5 $\phi$), and the test tube is set in an outer tube (inside diameter: 30 $\phi$), which is kept in a vessel of a constant temperature of 60° C for 30 minutes, and thereafter, it is further kept in a vessel of a constant temperature of 12° C, whereby the curve of time/temperature (i.e. the cooling curve) is measured. The result is shown in the accompanying FIG. 1. As is made clear from the test result, the mixtures 2 and 3, wherein the fractionated fats and oils are admixed with cacao butter in the ratio of 5 : 5 and 7 : 3 by weight, respectively, show a $\beta'$-type crystals-producing velocity similar to that of the cacao butter 4. The curve 1 in the FIG. 1 represents the fractionated fats and oils alone. From this test result, it is suggested that the fats and oils are useful for the cacao butter substitute.

In the present specification and claims, the 1,3-disaturated-2-unsaturated-triglycerides ($S_2U$) denote the triglycerides wherein the hydroxy group at 2-position is replaced by a monounsaturated fatty acid residue having 14 to 20 carbon atoms (referred to as $C_{14}$:1 – $C_{20}$:1) and the hydroxy groups at 1- and 3-positions are replaced by a saturated fatty acid residue having 16, 18 and/or 20 carbon atoms (referred to as $C_{16}$:0, $C_{18}$:0 and $C_{20}$:0, respectively).

The present invention is illustrated by the following Examples but is not limited thereto.

EXAMPLE 1

A 150 liter fermentation vessel provided with an agitator and an aeration duct is charged with a synthetic medium (100 liters) containing the following components:

Glucose — 40 g
$KH_2PO_4$ — 1 g
$MgSO_4 \cdot 7H_2O$ — 1 g
NaCl — 0.5 g
$CaCl_2 \cdot 2H_2O$ — 0.5 g
$FeCl_3$ — 2 mg
$ZnSO_4$ — 2 mg
Yeast extract — 3.6 g
Tap water — 1 liter (the medium is adjusted to pH 5.4 with sulfuric acid and then sterilized by heating at 120° C for 20 minutes). Into the medium is innoculated a pure culture of *Rhodosporidium toruloides* IFO 0413 (1,200 ml), and the mixture is cultivated under the conditions of aeration rate: 1 V.V.M. and temperature: 30° C for 48 hours.

After the cultivation, the culture broth contains the number of the microorganisms of about $8.97 \times 10^8$, and the weight of the cells (as the dried cells) is 12.77 g/liter. The culture broth is centrifuged to collect the cells and spray-dried to give beautiful red, dried cells (1,031 g, contents of the fats and oils: 59.8 % by weight, fat coefficient (F.C.): 19.1 %). The cells are pressed with a cage of a static pressure of 110 kg/cm² to separate the fats and oils. The residue is extracted twice with 5 times by volume of n-hexane. The solvent is evaporated from the extract (so-called "micells") and the residue is combined with the fats and oils to give the crude fats and oils (616 g), which show deep red color due to the calotenoid pigments contained therein and have the following chemical characteristics:

Acid value — 1.98
Iodine value — 70.2
Saponification value — 193.1
Fatty acid components:
  $C_{14}$:0 — 1.3% by weight
  $C_{16}$:0 — 25.0% by weight
  $C_{16}$–$C_{18}$:0 — 0.9% by weight
  $C_{18}$:0 — 12.7% by weight
  $C_{18}$:1 — 46.4% by weight
  $C_{18}$:2 — 11.7% by weight
  $C_{18}$:3 — 2.0% by weight
  $C_{20}$:0 — Trace
Triglyceride components:
  Trisaturated glycerides 2.5% by weight
  Disaturated glycerides
    2-saturated — 2.1% by weight
    2-unsaturated — 47.9% by weight
  Diunsaturated glycerides
    2-saturated — 0.5% by weight
    2-unsaturated — 39.0% by weight
  Triunsaturated glycerides — 8.0% by weight The fats and oils thus obtained are subjected to deacidification with an aqueous sodium hydroxide solution in a usual manner. The resultant product is dissolved in 4 times by volume of n-hexane and the mixture is stirred at −15° C for 60 minutes. The precipitated crystals are centrifuged and separated into the fractions as shown in the following Table 3.

Table 3

| Fraction | Iodine value | Melting (softening) point (° C) | Yield (%) |
|---|---|---|---|
| I Crystalline portion (high melting point portion) | 43.1 | 29.5 | 35.3 |
| II Filtrate portion (low melting point portion) | 79.4 | — | 64.7 |

The cooling curve of this crystalline portion is shown in the accompanying FIG. 1, as mentioned hereinbefore.

The crystalline portion (12 parts by weight), cacao butter (12 parts by weight), cacao mass (15 parts by weight), whole milk powder (20 parts by weight) and sugar (41 parts by weight) are mixed in a usual manner to give a chocolate, on which the tempering properties, the mold release characteristics and the antiblooming properties are tested. This composition shows the temperature tolerance of ± 2.0° C in case of the tempering and good mold release characteristics. Moreover, when the chocolate is repeatedly exposed to the different temperature atmospheres of 18° C and 30° C in a cycle of 12 hours (repeated 13 times), no blooming is observed, confirming the superior antiblooming properties of the chocolate.

EXAMPLE 2

The above Example 1 is repeated by using a 10 liter jar fermentor excepting that *Rhodosporidium torulides* IFO 0559 is used as the microorganism and the medium (6 liters) contains the following components:
- Glucose — 40 g
- L-Asparagine — 1.25 g
- Sodium glutamate — 1.05 g
- $KH_2PO_4$ — 1 g
- $MgSO_4.7H_2O$ — 1 g
- NaCl — 0.5 g
- $CaCl_2.2H_2O$ — 0.5 g
- $FeCl_3$ — 2 mg
- $ZnSO_4$ — 0.2 mg
- Vitamin $B_1$ — 0.3 mg (all components are dissolved in tap water (total: 1 liter), which is adjusted to a pH 5.4 with sulfuric acid and then sterilized at 120° C for 20 minutes).

After cultivating for 46 hours, the weight of the cells becomes 13.124 g/liter (as the dried cells). The content of the fats and oils is 56% by weight on the basis of the weight of the dried cells, and the fat coefficient is 18.3%.

The cells are separated by centrifuge, freeze-dried, ground together with quartz sand in a mortar, and then extracted with ether by using a Soxhlet extractor. The solvent is evaporated from the extract to give crude fats and oils (44.1 g, the acid value: 2.10, the iodine value: 73.4, the melting point: 19.1° C). The fats and oils have the following fatty acids components and the triglyceride components:

Fatty acid components:
- $C_{14}:0$ — 1.0% by weight
- $C_{16}:0$ — 24.1% by weight
- $C_{16}-C_{18}:0$ — 0.8% by weight
- $C_{18}:0$ — 12.5% by weight
- $C_{18}:1$ — 45.6% by weight
- $C_{18}:2$ — 12.7% by weight
- $C_{18}:3$ — 2.8% by weight
- $C_{20}:0$ — 0.5% by weight Triglyceride components:
- Trisaturated glycerides — 7.1% by weight
- Disaturated glycerides
  - 2-saturated — 9.1% by weight
  - 2-unsaturated — 30.1% by weight
- Diunsaturated glycerides
  - 2-saturated — 2.9% by weight
  - 2-unsaturated — 38.5% by weight
- Triunsaturated glycerides — 12.3% by weight The crude fats and oils obtained above show deep red color due to the calotenoid pigments contained therein. Accordingly, the cells are useful as a red pigment for foodstuffs.

EXAMPLE 3

A 500 ml flask is charged with Medium A or B (100 ml) as mentioned below. A pure culture of each strain (1.0 ml) as stated in the following Table 4 is innoculated. The mixture is subjected to a shaking culture under the conditions as mentioned in Table 4.

| Components of medium | Medium A | Medium B |
| --- | --- | --- |
| Glucose | 40 g | 40 g |
| $KH_2PO_4$ | 1 g | 1 g |
| $MgSO_4 . 7H_2O$ | 1 g | 1 g |
| NaCl | 0.5 g | 0.5 g |
| $CaCl_2 . 2H_2O$ | 0.5 g | 0.5 g |
| $FeCl_3$ | 2 mg | 2 mg |
| $ZnSO_4$ | — | 2 mg |
| Vitamin $B_1$ | — | 0.3 mg |
| Yeast extract | 1 g | 0.1 g |
| L-asparagine | — | 1.2 g |
| Urea | 0.5 g | — |
| Distilled water | 1 liter | 1 liter |
| pH value | 5.4 | 5.4 |

After the cultivation, the cells are collected by centrifuge, freeze-dried, and then the yield thereof is measured. Thereafter, the cells are ground together with quartz sand in a mortar, and then extracted with ether by using a Soxhlet extractor. On the fats and oils thus obtained, the yield, the chemical characteristics, the fatty acid components and the triglyceride components are measured. The results are shown in the following Table 4.

Table 4

| Microorganisms | Lipomyces starkeyi IFO 0678 | Lipomyces lipofer IFO 0673 | Rhodotorula graminis IFO 1422 |
| --- | --- | --- | --- |
| Medium | A | A | B |
| Cultivation temperature (° C) | 28 | 28 | 30 |
| Cultivation time (hour) | 72 | 72 | 72 |
| Yield | | | |
| Cells yield (g/l) | 11.32 | 10.77 | 8.54 |
| Fats and oils content (%) | 43.3 | 62.5 | 35.8 |
| Fat coefficient (%) | 13.2 | 21.7 | 10.0 |
| Chemical properties | | | |
| Acid value | 5.80 | 7.33 | 1.16 |
| Iodine value | 59.1 | 53.1 | 65.3 |
| Saponification value | 188.1 | 183.9 | 190.1 |
| Fatty acid components (%) | | | |
| $C_{14}:0$ | — | — | 1.0 |
| $C_{16}:0$ | 32.0 | 30.5 | 29.8 |
| $C_{16}-C_{18}:0$ | — | — | 1.8 |
| $C_{18}:0$ | 8.6 | 10.7 | 11.8 |

Table 4-continued

| | | | |
|---|---|---|---|
| $C_{18}:1$ | 54.1 | 54.1 | 35.5 |
| $C_{18}:2$ | — | — | 15.4 |
| $C_{18}:3$ | — | — | 3.9 |
| $C_{20}:0$ | 0.5 | 1.4 | 0.7 |
| Triglyceride components (%) | | | |
| Trisaturated glycerides | 2.5 | 2.6 | 3.7 |
| Disaturated glycerides | | | |
| 2-saturated | 3.8 | 3.2 | 4.8 |
| 2-unsaturated | 30.5 | 35.0 | 32.8 |
| Diunsaturated glycerides | | | |
| 2-saturated | 1.4 | 1.1 | 1.6 |
| 2-unsaturated | 45.0 | 43.8 | 43.0 |
| Triunsaturated glycerides | 16.5 | 14.3 | 14.1 |

| Microorganisms | Rhodotorula graminis NCYC 502 | Rhodotorula glutinis OUT 6151 | Rhodotorula glutinis AHU 3942 |
|---|---|---|---|
| Medium | B | B | B |
| Cultivation temperature (°C) | 30 | 30 | 30 |
| Cultivation time (hour) | 96 | 72 | 72 |
| Yield | | | |
| Cells yield (g/l) | 8.03 | 8.89 | 12.29 |
| Fats and oils content (%) | 41.4 | 37.8 | 33.6 |
| Fat coefficient (%) | 15.8 | 11.3 | 11.9 |
| Chemical properties | | | |
| Acid value | 2.01 | 1.91 | 2.01 |
| Iodine value | 66.3 | 68.6 | 68.8 |
| Saponification value | 188.9 | 190.8 | 191.3 |
| Fatty acid components (%) | | | |
| $C_{14}:0$ | 1.0 | 1.6 | 2.2 |
| $C_{16}:0$ | 26.8 | 29.8 | 28.8 |
| $C_{16}-C_{18}:0$ | 1.5 | 0.4 | 2.0 |
| $C_{18}:0$ | 11.9 | 9.0 | 7.7 |
| $C_{18}:1$ | 48.3 | 39.7 | 46.6 |
| $C_{18}:2$ | 8.0 | 15.8 | 8.7 |
| $C_{18}:3$ | 2.2 | 3.1 | 2.5 |
| $C_{20}:0$ | 0 | 0.3 | 1.5 |
| Triglyceride components (%) | | | |
| Trisaturated glycerides | 1.5 | 3.2 | 1.8 |
| Disaturated glycerides | | | |
| 2-saturated | 2.3 | 3.6 | 3.1 |
| 2-unsaturated | 31.7 | 31.5 | 30.4 |
| Diunsaturated glycerides | | | |
| 2-saturated | 0.8 | 1.7 | 1.3 |
| 2-unsaturated | 46.6 | 43.6 | 40.9 |
| Triunsaturated glycerides | 17.1 | 16.8 | 22.6 |

| Microorganisms | Endomyces vernalis IFO 0114 | Schizosaccharomyces probe IAM 4863 | Hansenula anomala NCYC 18 |
|---|---|---|---|
| Medium | B | B | B |
| Cultivation temperature (°C) | 25 | 30 | 30 |
| Cultivation time (hour) | 72 | 72 | 72 |
| Yield | | | |
| Cells yield (g/l) | 8.51 | 12.6 | 9.8 |
| Fats and oils content (%) | 30.9 | 8.9 | 15.8 |
| Fat coefficient (%) | 10.4 | 3.8 | 5.9 |
| Chemical properties | | | |
| Acid value | 5.41 | 3.42 | 3.34 |
| Iodine value | 65.9 | 109.2 | 98.4 |
| Saponification value | 185.0 | 179.0 | 184.7 |
| Fatty acid, components (%) | | | |
| $C_{14}:0$ | 1.9 | 0.2 | 0.4 |
| $C_{16}:0$ | 25.1 | 16.8 | 20.3 |
| $C_{16}-C_{18}:0$ | 7.1 | 1.1 | 2.9 |
| $C_{18}:0$ | 12.3 | 8.9 | 2.9 |
| $C_{18}:1$ | 47.1 | 72.0 | 47.6 |
| $C_{18}:2$ | 5.1 | 1.0 | 25.9 |
| $C_{18}:3$ | 1.4 | — | — |
| $C_{20}:0$ | 0 | — | — |
| Triglyceride components (%) | | | |

Table 4-continued

| | | | |
|---|---|---|---|
| Trisaturated | 1.9 | 0.6 | 0.6 |
| Disaturated glycerides | | | |
| 2-saturated | 2.9 | 2.4 | 2.6 |
| 2-unsaturated | 30.6 | 12.3 | 10.8 |
| Diunsaturated glycerides | | | |
| 2-saturated | 1.1 | 2.3 | 2.6 |
| 2-unsaturated | 46.7 | 43.6 | 32.3 |
| Triunsaturated glycerides | 17.7 | 38.7 | 41.1 |

What is claimed is:

1. A method for producing a cacao butter substitute, which comprises cultivating a *Rhodosporidium toruloides* microorganism capable of producing fats and oils rich in 1,3-disaturated-2-unsaturated triglycerides under an aerobic condition, collecting the resultant cells, and isolating a mixture containing fats and oils rich in 1,3-disaturated-2-unsaturated triglycerides from the cells.

2. The method according to claim 1, wherein the isolated mixture containing the fats and oils is subjected to fractionation.

3. The method according to claim 2, wherein the fractionation is carried out by (1) removing the trisaturated triglycerides having a higher melting point by precipitating them from the mixture, (2) separating a fraction containing the desired 1,3-disaturated-2-unsaturated triglycerides from the mixture as the second precipitate, and (3) removing the liquid fraction containing monosaturated-diunsaturated triglycerides and triunsaturated triglycerides from the second precipitate.

4. The method according to claim 3, wherein the 1,3-disaturated-2-unsaturated triglycerides containing-fraction contains at least 15% by weight of the 1,3-disaturated-2-unsaturated triglyceride components based on the weight of said fraction.

5. The method according to claim 1, wherein the cultivation is carried out at a temperature of from 20° to 37° C.

* * * * *